United States Patent [19]

Zardi et al.

[11] Patent Number: 4,963,338

[45] Date of Patent: Oct. 16, 1990

[54] PROCESS FOR HETEROGENEOUS SYNTHESIS AND RELATED REACTORS

[75] Inventors: Umberto Zardi, Via Lucino 57, CH-6932, Breganzona; Giorgio Pagani, Lugano, both of Italy

[73] Assignees: Ammonia Casale, S.A.; Umberto Zardi, Lugano, Switzerland

[21] Appl. No.: 213,369

[22] Filed: Jun. 30, 1988

[30] Foreign Application Priority Data

Jul. 3, 1987 [CH] Switzerland ............... 02529/87

[51] Int. Cl.⁵ ............... C01C 1/04; C07C 27/06
[52] U.S. Cl. ............... 423/360; 422/148; 422/192; 422/194; 423/361; 423/659; 518/712
[58] Field of Search ............... 423/360, 361, 659; 422/148; 518/712

[56] References Cited

U.S. PATENT DOCUMENTS

| | | | |
|---|---|---|---|
| 3,751,232 | 8/1973 | Borre et al. | 422/194 |
| 3,754,078 | 8/1973 | Hinrichs et al. | 422/148 |
| 3,957,449 | 5/1976 | Ciechowski | 423/360 |
| 4,101,281 | 7/1978 | Pagani | 422/148 |
| 4,181,701 | 1/1980 | Topsoe et al. | 423/360 |
| 4,346,060 | 8/1982 | Eagle et al. | 422/148 |
| 4,769,220 | 9/1988 | Zardi | 423/360 |
| 4,789,527 | 12/1988 | Osman et al. | 422/148 |

FOREIGN PATENT DOCUMENTS

| | | | |
|---|---|---|---|
| 12000734 | 2/1986 | Canada | 422/148 |
| 1914247 | 10/1970 | Fed. Rep. of Germany | 422/148 |
| 963951 | 2/1983 | U.S.S.R. | 423/360 |

Primary Examiner—Wayne A. Langel
Attorney, Agent, or Firm—Ostrolenk, Faber, Gerb & Soffen

[57] ABSTRACT

Improved process for heterogeneous synthesis and related reactors according to which the synthesis catalyst is distributed in three catalytic beds either axial-radial or radial, control of the temperature between beds being effected by means of fresh quench gas between the first and the second bed and by means of indirect cooling with an exchanger between the second and the third bed of the gas leaving the second bed, using fresh gas which is heated inside the tubes of said exchanger.

5 Claims, 5 Drawing Sheets

PROCESS FOR HETEROGENEOUS SYNTHESIS AND RELATED REACTORS

The importance of achieving high reaction yields in the heterogeneous synthesis for the production of ammonia, methanol and other products is well known.

Such reaction yields are remarkably influenced by: (a) the optimization of the number of catalytic beds; (b) the system to control reaction temperature by means of intermediate cooling of the gas between catalytic beds; (c) the efficiencY of the catalyst usually selected with a small granulometry (1.5÷3 mm) in the more advanced radial or axial-radial reactors.

There is a great number of reactors of the old generation in existence with axial flow of the gas in the catalytic beds, so that large granulometry (6+12 mm) not very efficient catalyst must be used, with the inconvenient of low yields and considerable pressure drop and therefore high energy consumption.

The above reactors have usually several catalytic beds (up to four in the case of Kellogg reactors) with intermediate quenching between beds (mixing the hot reacted gas with cooler feed gas).

In the more advanced reactors the flow of gas through the catalytic beds is either radial (reactors such as Topsoe or Uhde) or axial-radial such as in the Ammonia Casale reactor. In these reactors more active catalyst with a small granulometry is generally used (1.5+3 mm in cartridges with two or three radial or axial-radial beds, with the advantage of low pressure drop, with intermediate cooling between the beds by means of the indirect exchange of heat using an exchanger.

The advantage of indirect exchange over quenching is that it permits a fuller use of the catalytic beds, and therefore in the above reactors higher conversion yields are obtained, hence lower energy consumption.

A remarkable interest has been shown recently in the modernization of existing axial reactors with low yields in order to improve their performance up to the level of more modern radial or axial-radial reactors.

The Applicant has recently put forward in his European patent application 86104911 the modification of axial reactors with several beds, such as Kellogg reactors for example, to turn them into more efficient axial-radial or radial reactors. According to the above patent application the cartridge of existing reactors is simply modified "in situ" (keeping therefore most of the original cartridge) by adding walls permeable by gas and bottoms in order to turn axial beds into axial-radial or radial beds. According to the above application various cartridge arrangements can be achieved.

A drastic modification of the existing cartridge is necessary, on the other hand, to convert the cartridge into two catalytic beds with intermediate indirect cooling between beds by means of an exchanger, according to the Topsoe plan in "Nitrogen". Said plan requires besides the use of an expensive large size exchanger in high-quality material (Inconel 600) because of the high temperatures.

Continuing in his research the Applicant has surprisingly conceived a system which can be suitable adopted to modify existing reactors as well as for new reactors according to which the synthesis catalyst is distributed in three axial-radial or radial catalytic beds, control of the temperature being effected by quenching with fresh gas between the first and the second bed and by means of indirect cooling with exchanger between the second and the third bed of the gas leaving the second bed using fresh gas heated inside the tubes of said exchanger.

In the Drawings

The above system, although it minimizes modifications to the cartridge when modernizing existing reactors, permits further increase of reaction yields when compared to the state of the art described in the Applicant's application 86104911.2 and in the "Nitrogen" article, avoiding use of a big exchanger in high-quality material such as Inconel 600. According to the new system, in effect, the exchanger required to control temperature between the second and the third bed can be much smaller (70%) and in a standard material such as stainless steel.

According to a particular embodiment of the invention (FIG. 1) the gas running through the catalytic beds with an axial-radial or radial flow runs: (a) from the inside towards the outside of the bed in the first catalytic bed, the fresh quench gas between the first and the second catalytic bed being distributed from an annular distributor situated in the top section of the external gas collector; (b) from the outside towards the inside of the bed in the second and third catalytic bed an exchanger being situated in the central part of the second catalytic bed, said exchanger being fed from a portion of the fresh feed gas flowing through the exchanger inside the tubes, and from the other outside the tubes by the hot gas coming from the second bed.

Figure 2:
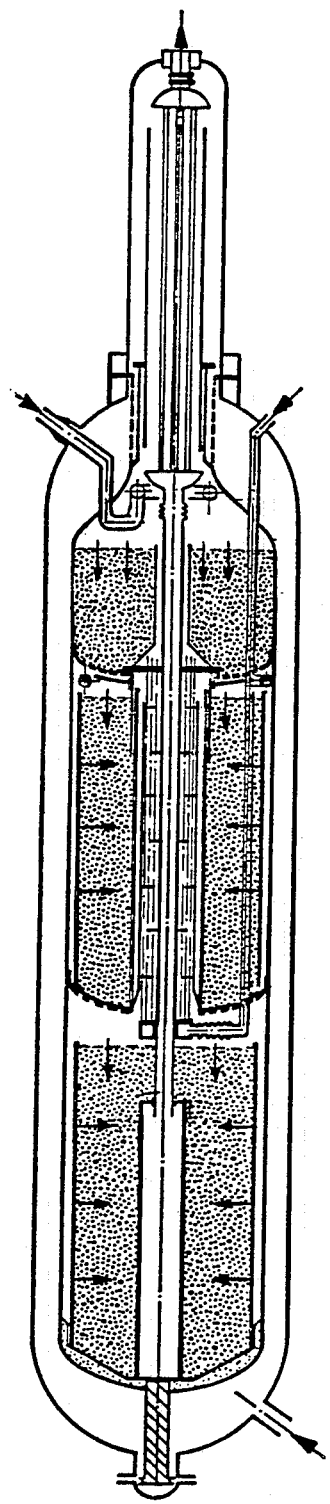
FIG. 2 shows an embodiment wherein the first catalytic bed is run through by the synthesis gas with an axial flow.

According to a variation of the above-mentioned possible embodiment of the invention, the first catalytic bed is run through by the gas with an axial flow, the annular distributor of the quench gas being situated near the external wall of the cartridge in the higher part of the bottom of the first bed, according to the description made in the Applicant's Swiss application No. 02221/86-7 (FIG. 2).

According to a further variation of the invention (FIG. 3) the gas flows in the three beds with a radial flow.

The advantages of the above-mentioned invention over the state of the art can be summed up as follows:
I—high yields
II—minimum investment
III—minimum modification in the case of modernization "in situ" of existing reactors.

Figure 1:
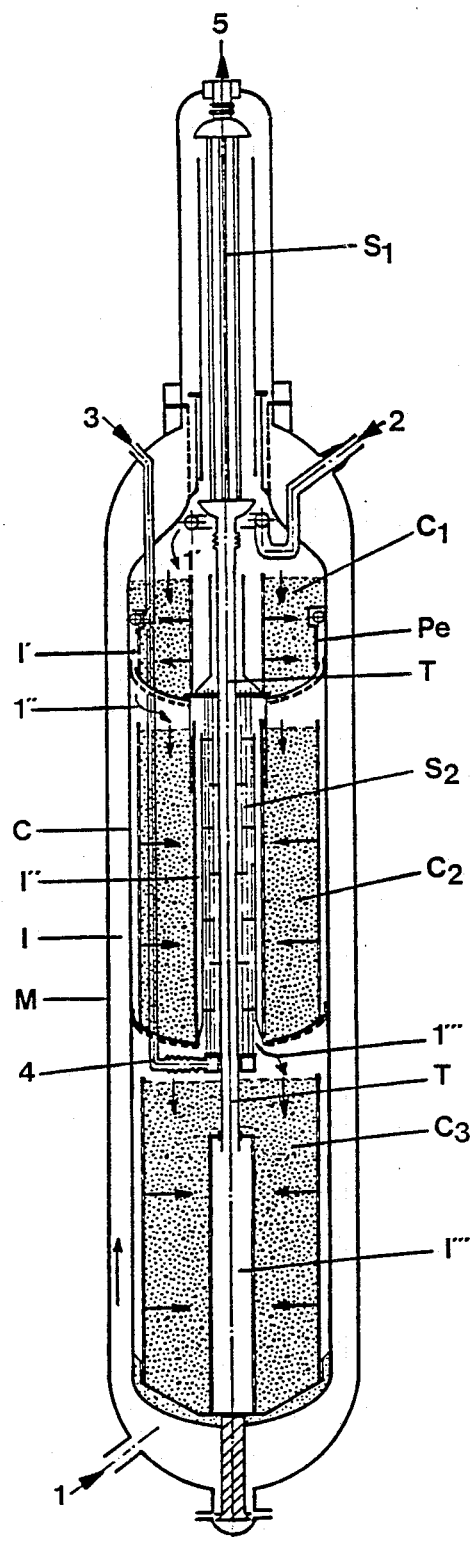
FIG. 1 shows an embodiment wherein the synthesis gas runs through the catalytic beds with an axial-radial or radial flow.

For the purpose of illustration but not of limitation some embodiments of the invention are described:

In FIG. 1 shows schematically a synthesis reactor cartridge with three catalytic beds with axial-radial flow of the gas normally adopted when modernizing "in situ" existing reactors. Most of the stream 1 feed gas enters from the bottom of the reactor's shell M, runs from bottom to top along airspace I between the shell and the cartridge C and goes then to the outside of the exchanger S1 to be pre-heated by the hot gas leaving from the head of the reactor, stream 5.

The gas so pre-heated stream 1', whose temperature is controlled by a part of the feed gas stream 2, mixes with stream 4 pre-heated in exchanger S2 and reaches the first catalytic bed through which it runs with an axial-radial flow from the inside outwardly, collecting in airspace I' between cartridge C and the outside wall Pe of the first bed where it mixes with the fresh quench gas stream 3. The gas so mixed to a lower temperature stream 1" reaches the second catalytic bed through which it runs reacting and heating up with an axial-radial flow from the outside towards the inside of the bed. The hot gas collects then in air-space I" formed by the inside wall of the catalytic bed and by the outer shell of exchanger S2 situated in the central part of the second catalytic bed and is cooled running from top to bottom outside the tubes of exchanger S2, finally collecting at the exchanger's exit to reach the entrance to the third catalytic bed, stream 1'''.

A stream of fresh gas 4 is fed to the bottom of exchanger through which it runs inside the tubes pre-heating and finally joining stream 1'. Stream 1''' finally runs with an axial-radial flow from the outside to the inside through the third catalytic bed C3, collecting in the central collector I''' whence through the central transfer tube T it reached the inside of the tubes of exchanger S1 where it cools preheating stream 1 finally to leave the converter, stream 5.

Figure 3:
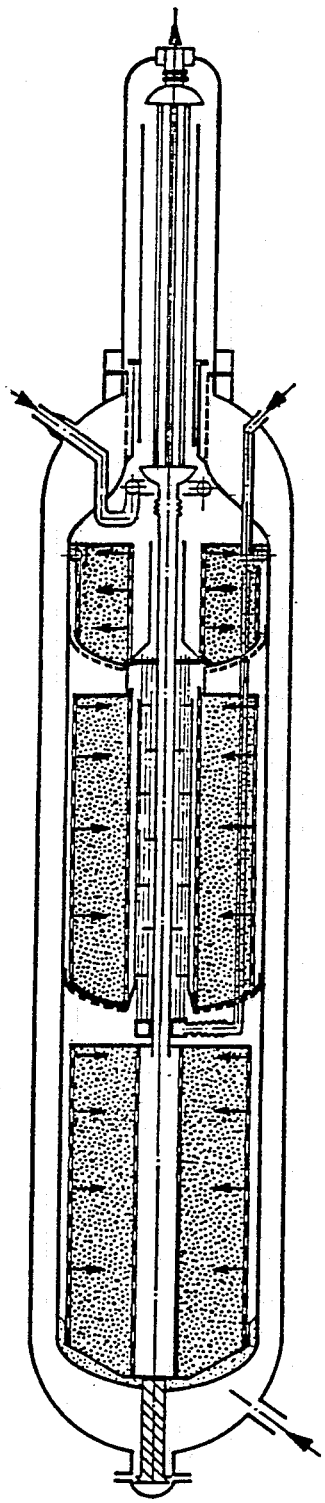
FIG. 3 show an embodiment wherein the synthesis gas flows in the three beds with a radial flow.

FIG. 3 shows the cross-section of a synthesis reactor's cartridge with three catalytic beds with the gas flowing radially. Exception made for the flow of the gas in the beds, which in this instance is radial and not axial-radial as in FIG. 1, the beds being closed at the top, the gas run through the various parts of the reactor is as previously described for FIG. 1.

Example

With reference to FIG. 1 the following is an example of embodiment of the invention concerning this application.

In a synthesis reactor for the production of 1000 MTD of ammonia the following operating conditions apply:

pressure at reactor's inlet: 140 bar

|  | Rate of flow |  | Temperature |
|---|---|---|---|
| stream 1 | 7970 Kmol/h | 41.0% | 143° C. |
| stream 2 | 0 Kmol/h | — | 143° C. |
| stream 3 | 6069 Kmol/h | 31.3% | 143° C. |
| stream 4 | 5384 Kmol/h | 27.7% | 143° C. |
| stream 5 | 16992 Kmol/h | — | 352° C. |

| Composition of streams 1, 2, 3, 4 | Composition of stream 5 |
|---|---|
| H2 66.68% mol | H2 54.68% mol |
| N2 22.22% mol | N2 18.22% mol |
| CH4 4.70% mol | CH4 5.38% mol |
| A 4.30% mol | A 4.92% mol |
| NH3 2.10% mol | NH3 16.80% mol |

Figure 4A:
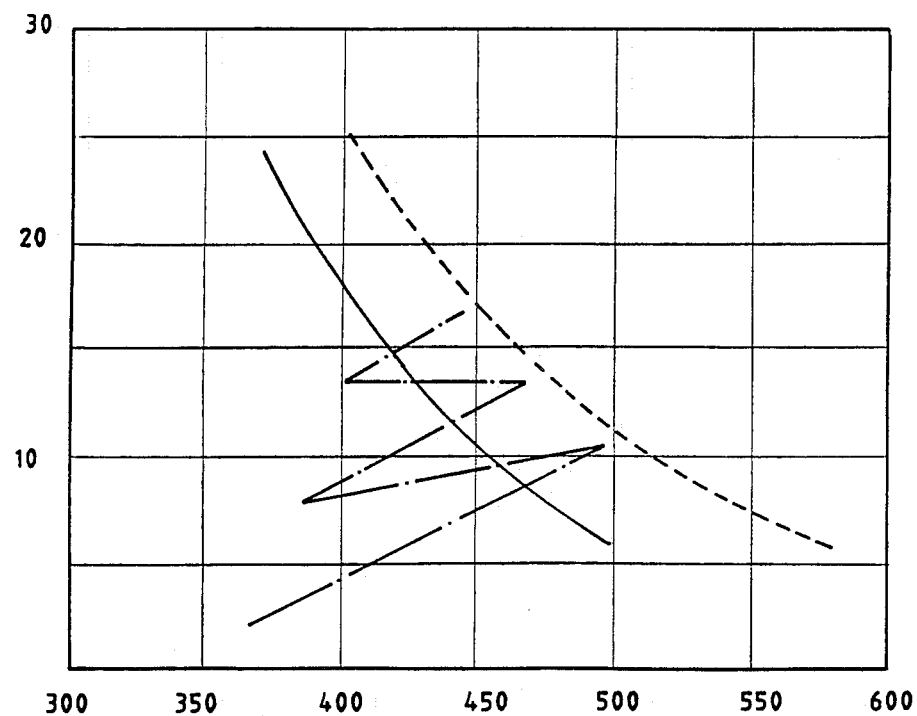
FIG. 4 shows the diagram temperature/reactor's yield (FIG. 4a) and the diagram temperature/state of the art yields (FIG. 4b and FIG. 4c).
Figure 4B:
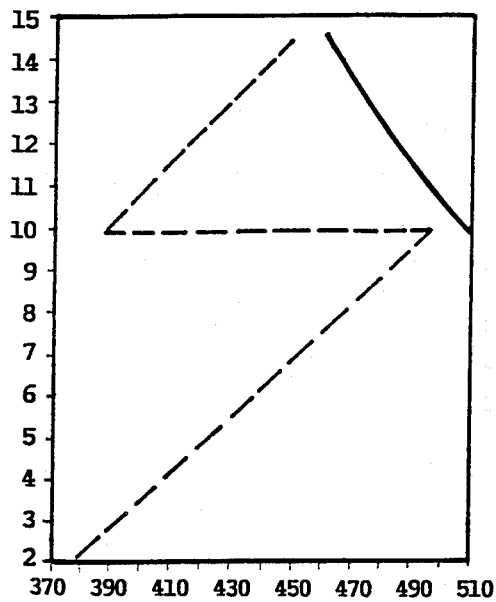
Figure 4C:
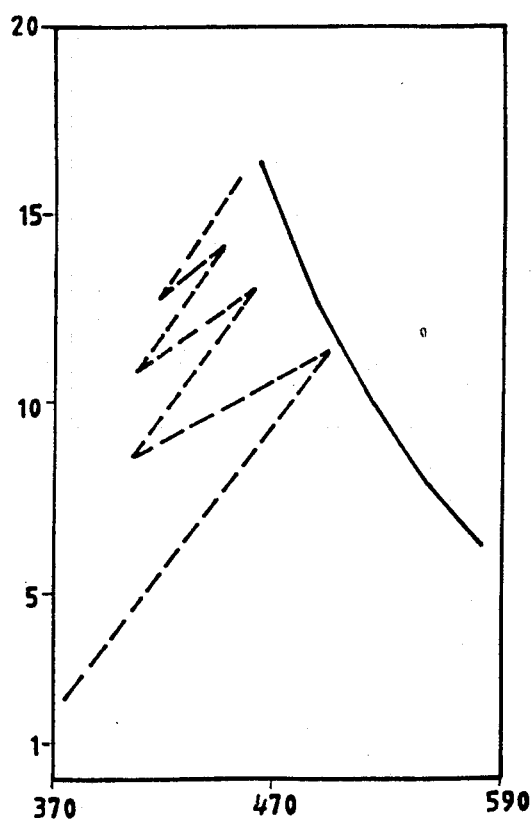

FIG. 4 shows the diagram temperature/reactor's yield under the operating conditions described above (FIG. 4a) and the diagrams temperature/state of the art yields described in FIG. 2 and FIG. 7 of "Nitrogen" (FIG. 4b and FIG. 4c). As the above-mentioned diagrams show, the improvement in yield obtained with the reactor described according to the invention is about 25 to 60% above the yield obtained in the state of the art.

In the above-mentioned diagrams gas temperature is given in abscissa and the concentration of ammonia at reactor's outlet in ordinate.

We claim:

1. A process for heterogeneous synthesis wherein synthesis catalyst is distributed in three axial-radial or radial catalytic beds, and the temperature between the beds is controlled by quenching with fresh gas between the first catalytic bed and the second catalytic bed and by indirect cooling of the gas leaving the second catalytic bed with fresh gas heated inside the tubes of a heat exchanger disposed between the second catalytic bed and the third catalytic bed.

2. A process according to claim 1, wherein the gas running through the catalytic beds with an axial-radial or radial flow, runs: (a) from the inside to the outside of the bed in the first catalytic bed; and (b) from the outside to the inside of the bed in the second and third catalytic beds, the heat exchanger being disposed in the central part of the second catalytic bed.

3. A process according to claim 1, wherein the gas runs through the first catalytic bed with an axial-radial flow and through the remaining two beds with an axial-radial or radial flow, from the inside towards the outside of the beds.

4. A process according to claim 2, wherein the gas running through the catalytic beds with axial-radial or radial flow, runs: (a) from the inside towards the outside of the bed in the first catalytic bed, the fresh quench gas introduced between the first and the second bed being distributed by an annular distributor situated in the top section of an external gas collector; and (b) from the outside towards the inside of the bed in the second and third catalytic beds, the exchanger being disposed in the central part of the second catalytic bed, the exchanger being fed at one the tubes, and at the other end outside the tubes by the hot gas coming from the second bed.

5. A process according to claim 1, wherein the flow fresh quench gas is at least 20% of the total flow of feed gas, the flow of fresh gas being fed inside the exchanger tubes being at least 20% of the total feed gas flow.

* * * * *